United States Patent
Koerner (10) Patent No.: US 11,052,203 B2
(45) Date of Patent: Jul. 6, 2021

(54) PHARMACEUTICAL DISPENSER WITH A DETECTION DEVICE

(71) Applicant: APTAR RADOLFZELL GMBH, Radolfzell (DE)

(72) Inventor: Joachim Koerner, Uhldingen-Muehlhofen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 1143 days.

(21) Appl. No.: 15/123,056

(22) PCT Filed: Mar. 10, 2015

(86) PCT No.: PCT/EP2015/054981
§ 371 (c)(1),
(2) Date: Sep. 1, 2016

(87) PCT Pub. No.: WO2015/150029
PCT Pub. Date: Oct. 8, 2015

(65) Prior Publication Data
US 2017/0014583 A1    Jan. 19, 2017

(30) Foreign Application Priority Data

Apr. 2, 2014  (DE) ..................... 10 2014 206 350.7

(51) Int. Cl.
*A61M 15/00* (2006.01)
*A61M 16/00* (2006.01)

(52) U.S. Cl.
CPC ........ *A61M 15/008* (2014.02); *A61M 15/009* (2013.01); *A61M 15/0021* (2014.02);
(Continued)

(58) Field of Classification Search
CPC ............ A61M 15/0021; A61M 15/008; A61M 15/009; A61M 2016/0027; A61M 2205/3331; A61M 2207/00
(Continued)

(56) References Cited

U.S. PATENT DOCUMENTS 5,505,192 A * 4/1996 Samiotes ............ A61M 15/009
128/200.14
5,544,647 A * 8/1996 Jewett ................. A61M 15/009
128/200.23
(Continued)

FOREIGN PATENT DOCUMENTS

DE    10 2010 024 912 A1   12/2011
DE    10 2013 214 601 B3   5/2014
(Continued)

OTHER PUBLICATIONS

International Search Report issued in Application No. PCT/EP2015/054981 with English translation dated May 28, 2015 (6 pages).
(Continued)

*Primary Examiner* — Rachel T Sippel
*Assistant Examiner* — Kelsey E Baller
(74) *Attorney, Agent, or Firm* — Flynn Thiel, P.C.

(57) ABSTRACT

A pharmaceutical dispenser with a housing, a medium reservoir, a discharge opening, connection channel connecting the medium reservoir to the discharge opening, and a detection device arranged in the area of the connection channel and designed to detect medium flowing therein. The connection channel is connected to and communicates with a pressure chamber, the detection device includes a membrane which delimits the pressure chamber, and includes an electrically conductive connection portion and is subjected to pressure. The detection device has an electrical mating contact surface in relation to which a membrane-side con-
(Continued)

nection portion is movable when subjected to pressure, such that an electrical contact between the conductive connection portion and the mating contact surface is established or cancelled.

22 Claims, 4 Drawing Sheets

(52) U.S. Cl.
CPC ........... *A61M 2016/0027* (2013.01); *A61M 2205/3331* (2013.01); *A61M 2207/00* (2013.01)

(58) Field of Classification Search
USPC ............ 128/203.12, 200.11–200.14, 200.23
See application file for complete search history.

(56) References Cited

U.S. PATENT DOCUMENTS

| | | | |
|---|---|---|---|
| 5,826,571 A | 10/1998 | Casper et al. | |
| 6,357,442 B1 | 3/2002 | Casper et al. | |
| 6,672,304 B1 | 1/2004 | Casper et al. | |
| 6,729,324 B2 | 5/2004 | Casper et al. | |
| 8,215,299 B2 * | 7/2012 | Wu | A61M 15/009 128/200.23 |
| 8,746,238 B2 | 6/2014 | Kohnle | |
| 8,869,791 B2 * | 10/2014 | Sauzade | G01F 13/008 128/200.14 |
| 9,872,964 B2 * | 1/2018 | Cline | A61M 15/009 |
| 2002/0100472 A1 | 8/2002 | Casper et al. | |
| 2005/0028815 A1 * | 2/2005 | Deaton | A61M 15/008 128/200.23 |
| 2007/0017506 A1 * | 1/2007 | Bell | A61M 15/009 128/200.23 |
| 2011/0303221 A1 | 12/2011 | Kohnle | |
| 2016/0144091 A1 * | 5/2016 | Breedon | A61F 2/0036 623/3.29 |
| 2016/0166783 A1 | 6/2016 | Kohnle et al. | |

FOREIGN PATENT DOCUMENTS

| | | | |
|---|---|---|---|
| EP | 2 397 178 A1 | | 12/2011 |
| GB | 2470188 A | | 11/2010 |
| GB | 2470188 | * | 5/2011 |
| WO | WO 97/33640 A1 | | 9/1997 |
| WO | WO 2005/009325 A2 | | 2/2005 |

OTHER PUBLICATIONS

Written Opinion of International Searching Authority issued in Application No. PCT/EP2015/054981 dated May 28, 2015 (5 pages).

* cited by examiner

PHARMACEUTICAL DISPENSER WITH A DETECTION DEVICE

FIELD OF APPLICATION AND STATE OF THE ART

The invention relates to a pharmaceutical dispenser with a housing, with a medium reservoir, with a discharge opening and with a connecting duct which connects the medium reservoir to the discharge opening. A generic dispenser further exhibits a detection device which is arranged in the region of the connecting duct and is designed to detect the medium flowing in the connecting duct.

Generic dispensers are utilized for the purpose of discharging pharmaceutical media, in particular pharmaceutical liquids. In particular, generic dispensers can take the form of inhalers and serve for generating a nebulized stream of medium for the purpose of inhalation.

In generic dispensers, a detection device is provided which in response to a discharge process is capable of recognizing said process and of processing it electronically or of relaying it as a signal to a processing device for electronic processing. This processing may, in particular, have the aim of counting the discharge processes that have occurred, in order to estimate how many discharge processes are still possible with the dispenser or, to be more exact, with the medium reservoir employed in the dispenser. This information is of great importance for patients, in order to be able to estimate whether they can manage with the remaining quantity of pharmaceutical medium or require a new dispenser or a new medium reservoir for the dispenser.

From the state of the art it is known, in particular, to detect and count the manual actuation of the dispenser itself. However, it has been shown in the past that such a detection may be disadvantageous, since in this case both uncounted discharge processes and counted actuation processes that have not caused a discharge may occur.

It has therefore already been proposed not to detect the displacement of mechanical parts of the dispenser that are displaced with respect to one another in the course of a discharge operation, but instead to detect a physical quantity that is directly related to the outflowing medium. Such a dispenser is known from DE 10 2013 214 601 B3, in which in the region of the connecting duct a pressure chamber is provided which is intermittently bounded by a deformable membrane. When the medium flows through the connecting duct, it increases the pressure here and consequently deflects the membrane. This deflection is utilized to actuate a push-button, the actuation of which is, in turn, counted by the counter.

OBJECT AND SOLUTION

It is an object of the invention to develop a generic dispenser such that said dispenser permits an evaluation of the discharge processes particularly reliably.

In accordance with this purpose, there is provision that the connecting duct is connected in a communicating manner to a pressure chamber. The detection device includes a membrane which bounds this pressure chamber at least intermittently and is capable of being deflected by a rise in pressure in the pressure chamber. The membrane provided includes an electrically conductive connecting portion which is integrated into the membrane or fastened thereto in such a way that in the event of a deflection of the membrane it is deflected together with the latter.

The detection device is designed to interact with this connecting portion and for this purpose is provided with at least one electrical mating contact surface, with respect to which the membrane-side connecting portion is capable of being displaced by application of pressure to the membrane. The mating contact surface and the connecting portion on the membrane are arranged in relation to one another in such a way that by virtue of the pressure-induced deformation of the membrane a contact between the conductive connecting portion of the membrane and the mating contact surface can be created or broken.

In a pharmaceutical dispenser there is consequently provision that in the region of the connecting duct, through which the medium flows in the direction of the discharge opening, a pressure chamber is provided which is either connected in communicating manner to said connecting duct, branched off from a main duct, or is a direct part of the connecting duct. This pressure chamber is sealed on one side by the reversibly deformable elastic membrane which enables a variability of the internal volume of the pressure chamber. If medium flows through the connecting duct, the pressure within the pressure chamber increases, and the membrane is deflected.

The connecting portion which is moved jointly with the membrane is electrically conductive and thereby capable of permitting a switching signal when, as a consequence of the deflection or the return from the deflected state, it comes into contact with the mating contact surface or detaches from it. Unlike in the case of the exemplary embodiment presented in the aforementioned DE 10 2013 214 601 B3, no push-button provided with a separate restoring means such as a spring has to be actuated. Instead of this, the current required for the switching pulse is conducted directly through the membrane or through the connecting portion which is moved jointly with the membrane. This enhances the reliability of detection, since a lower pressure may already suffice for reliable generation of a pulse.

The stated detection device is preferentially connected to an electronic evaluating device which, in particular, may take the form of an electronic counter. This evaluating device makes two signal lines available. The evaluating device is preferentially designed to interpret a materializing connection of the signal lines, starting from an electrical separation of these two signal lines, as a pulse, and in response thereto to carry out an evaluating process, in particular a counting process. Instead of the connecting of the previously separated signal lines, the separating of the previously connected signal lines may also be evaluated in this manner.

A particularly advantageous design of the detection device provides that the latter exhibits two electrical mating contact surfaces which are respectively connected to one of the two signal lines of the electronic evaluating device. These mating contact surfaces are fixed in relation to one another and are designed to be initially electrically isolated with respect to one another. They are arranged in such a manner that they can be electrically connected to one another by deflection of the membrane-side electrically conductive connecting portion. Alternatively, they can also be connected to one another by the return of the electrically conductive connecting portion from the deflected state of the membrane. The membrane or the connecting portion provided thereon acts as an electrical bridge in such a design.

In an alternative design, the electrical mating contact surface is connected to one signal line, whereas the other signal line is permanently connected to the membrane or to the connecting portion provided thereon. Unlike in the case of the preceding design, in which the connecting portion comes into contact as intended with both mating contact surfaces and then acts as a bridge, in the case of the last-named variant the membrane-side connecting portion has to come into contact with only one mating contact surface as a result of the deflection. The membrane-side connecting portion is permanently coupled with the other signal line, so that a processing pulse or counting pulse already occurs by virtue of the contact of the membrane-side connecting portion with the only one mating contact surface.

In order to make the membrane at least intermittently electrically conductive in the manner described, several design options are expedient. According to a first variant, the membrane is formed in multiple layers and includes at least one plastic layer and at least one electrically conductive connecting layer, different from said plastic layer, which forms the conductive connecting portion. By virtue of the two-layered or multi-layered structure, the membrane is able to satisfy all the stipulated requirements particularly well. The conductive connecting layer can form the desired contact with low resistance, whereas the preferentially non-conductive plastic layer can be optimized with regard to the deformation properties and restoring properties of the membrane. In such a two-layered or multi-layered membrane, the connecting layer extends over the entire surface of the membrane.

In a second alternative, the membrane is provided merely in a contact region with an electrically conductive connecting portion which, for example, could be present in the manner of a small metallic lamina which has been connected to the membrane by an adhesive bond or has been encapsulated by said membrane by injection molding.

A third alternative provides that the membrane exhibits at least one layer of an electrically intrinsically conductive plastic or has been manufactured as a whole from such a plastic. Such intrinsically conductive plastics require no additive in order to create an electrical connection. However, they have a comparatively high resistivity, so that the electronic evaluating device has to have a comparatively high sensitivity.

Instead of an intrinsically conductive plastic, by means of conductive fillers, it is also possible to make conductive overall a plastic that is not conductive as pure plastic. This can be done through the incorporation of graphite, for example.

The membrane may take the form of a separate component which in edge regions is connected to the housing of the dispenser, in order to seal an opening of the pressure chamber that is not sealed by the housing. Particular advantages with regard to the imperviousness and the production costs can be achieved if non-deformable portions of the housing, in particular non-deflectable walls of the pressure chamber and/or of the connecting duct, on the one hand, and the membrane or at least one layer of the membrane, on the other hand, have been manufactured in one piece from a matching plastic. The deflection capability of the membrane is achieved in this case by the thin-walled nature of the plastic. It may likewise be advantageous to manufacture the housing or at least component portions of the housing, on the one hand, and the membrane, on the other hand, in one piece by multi-component injection molding. In this connection, housing portions and the membrane are produced from different plastic materials in a two-stage injection-molding process with a variable cavity. In a contact region, however, the second plastic melts first, so that a particularly intimate and tight connection comes about. The multi-component injection molding is advantageous, in particular, when the membrane consists at least partly of an intrinsically conductive plastic or of a plastic made conductive by fillers.

Membranes can in principle be produced most easily by being extruded, resulting in a uniform membrane thickness. However, it is particularly advantageous if the membrane is produced by injection molding of plastic or by another method that permits the membrane to be provided with a variable thickness or to be provided with at least one bead. By virtue of a deviation of the membrane from the constant thickness or from the purely flat shape, reinforcements and/or regions of facilitated deformability can be created which can contribute to a more defined deformation of the membrane. By this means, it is made easier to bring the membrane into contact with the mating contact surface(s) in planar manner.

BRIEF DESCRIPTION OF THE DRAWINGS

Further advantages and aspects of the invention will become clear from the exemplary embodiments described in the following, which will be elucidated on the basis of the figures. Shown in these figures are:

FIG. 1 the basic structure of an embodiment of a dispenser according to the invention in a partly sectional view, FIGS. 2a and 2b a detection device for detecting discharge processes before and during a discharge process, FIG. 3 two mating contact surfaces, arranged on a printed circuit board, for interacting with a membrane of the dispenser shown in FIGS. 1 to 2b, FIGS. 4a to 4e various configurations of the membrane of the dispenser shown in FIGS. 1 to 3 and FIGS. 5a, 5b and 6 a further variant with only one mating contact surface, with respect to which the membrane is mobile.

DETAILED DESCRIPTION OF THE EXEMPLARY EMBODIMENTS

Figure 1:
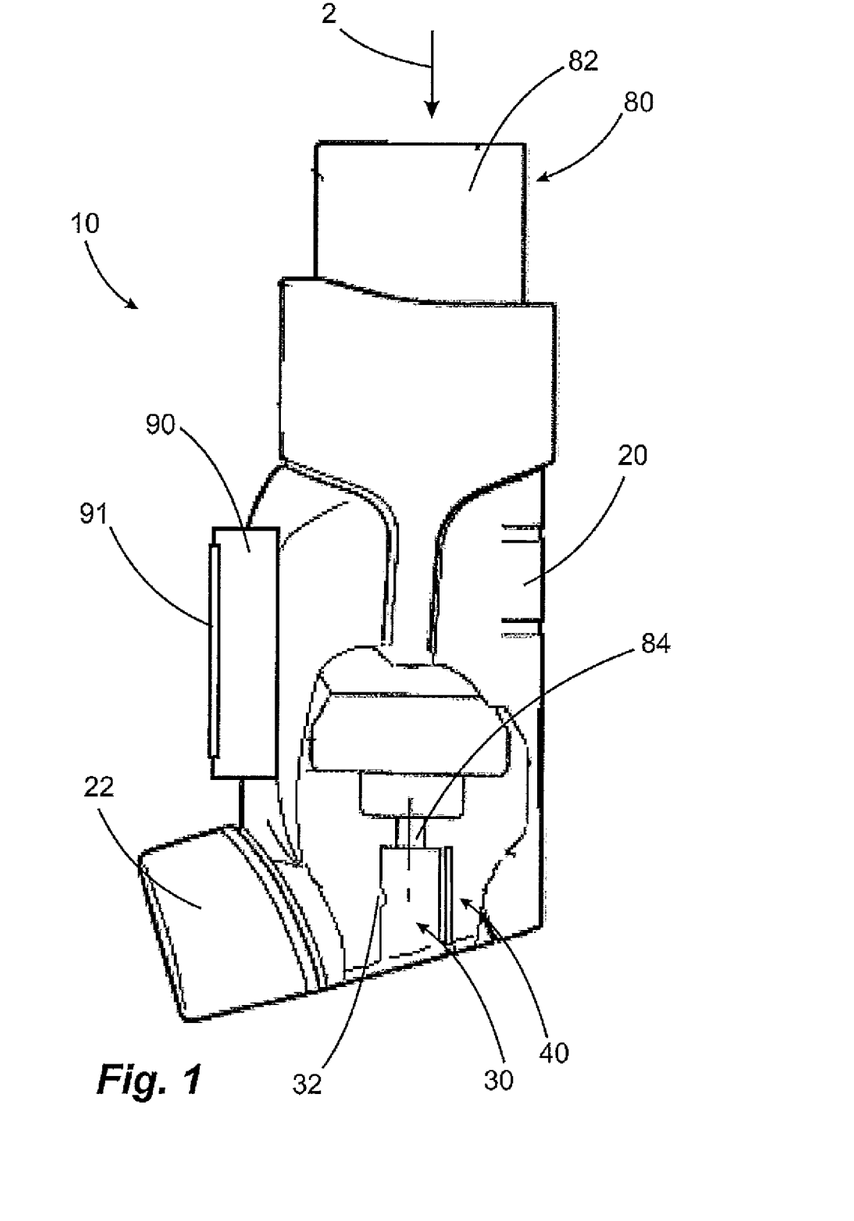

FIG. 1 shows, in a schematic view, a dispenser 10 according to the invention. Said dispenser takes the form of an inhalation dispenser. Such dispensers are ordinarily designated as MDI or PMDI.

The dispenser 10 is provided with a housing 20, into which a container unit 80 has been inserted. This container unit 80, in turn, is provided with a medium reservoir 82 and also an outlet nozzle 84 which is displaceable with respect to the medium reservoir 82 and in the course of such a displacement emits a measured quantity of medium through an exit duct in the outlet nozzle 84. The container unit 80 has been inserted into the housing 20 from above, so that the outlet nozzle 84 projects into a bottom-side receptacle 30. By depression of the reservoir medium 82 in the direction of the arrow 2, a discharge process can consequently be brought about which has the result that medium is output from the medium reservoir 82 through a discharge opening 32 of the receptacle. This happens while the user is inhaling through a mouthpiece 22 of the housing 20. The medium emitted through the discharge opening 32 mixes with the air aspirated by the user and in this way gets into the lungs of the user as intended.

The dispenser 10 is provided with a detection device 40 and an evaluating device 90 which takes the form of an electronic counter. This counter 90 receives a counting pulse from the detection device 40 when medium is being conveyed from the medium reservoir 82 to the discharge opening 32. By the counting of the discharge processes and the representing of the current level on a display 91, it is possible for the user to estimate the remaining filling volume in the medium reservoir 82 and consequently to avoid unexpectedly having no more medium available.

Figure 2A:
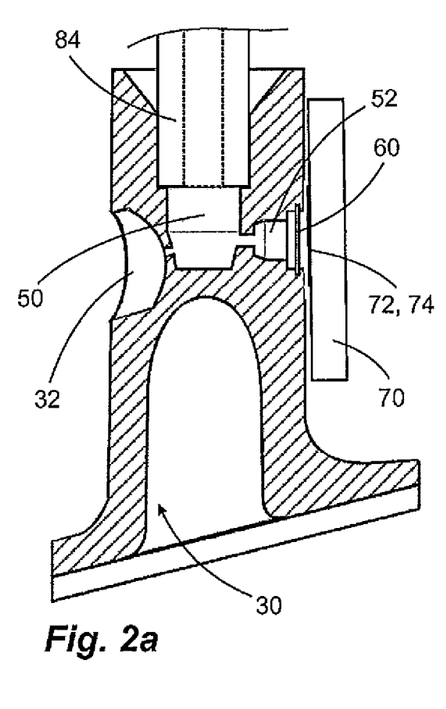
Figure 2B:
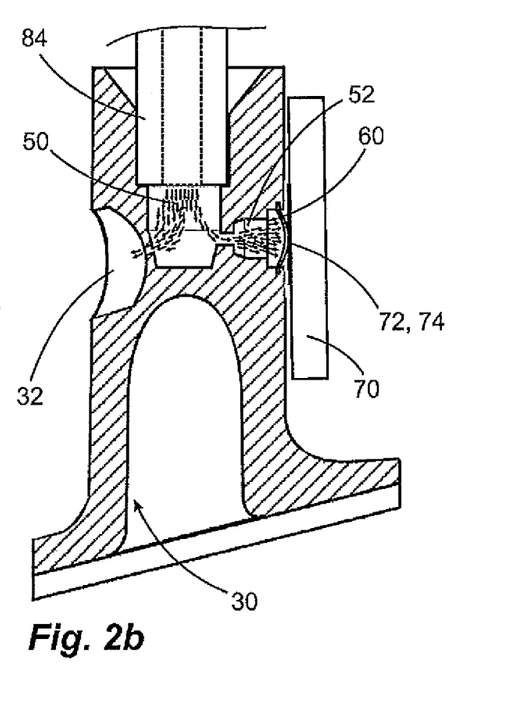

FIGS. 2a and 2b show the detection device 40 in enlarged form. As can be gathered from the stated figures, a connecting duct 50 is provided within the receptacle 30 for the outlet nozzle 84. Said connecting duct 50 is provided with a branched pressure chamber 52 in which the pressure rises when medium is flowing from the outlet nozzle 84 to the discharge opening 32 in the manner represented in FIG. 2b.

Figure 3:
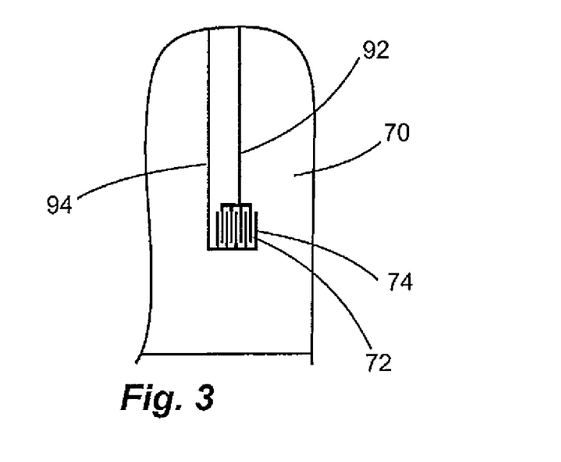

The pressure chamber 52 is bounded on one side by a membrane 60 which is deformed in the manner represented in FIG. 2b when there is an excess pressure in the pressure chamber 52. On the outside of the pressure chamber, a printed circuit board 70 is provided. On this printed circuit board 70, which is represented once again in FIG. 3, two contact surfaces 72, 74 are affixed which are respectively connected to a signal line 92, 94. Said signal lines 92, 94 are, in turn, coupled with the evaluating device 90 in a manner not represented in any detail. The metallic contact surfaces 72, 74 are arranged to be interleaved in a comb-like manner, so that in each instance several component portions of these contact surfaces are immediately adjacent to one another. At the same time, however, the contact surfaces are galvanically isolated from one another.

The membrane 60 is designed to be electrically conductive at least on its side pointing in the direction of the contact surfaces 72, 74. When the membrane is deflected in the manner illustrated in FIG. 2b, it is applied onto and connects the contact surfaces 72, 74 interleaved in a comb-like manner. The signal lines 92, 94 are connected by this means. This can be detected by the evaluating device 90, and in response thereto a counting step can be performed. The updated value that provides information about the doses already emitted or still remaining in the medium reservoir 82 is subsequently represented on the display 91.

By virtue of the fact that the membrane itself closes the contact, and a mechanical action on further components for the purpose of displacing the same is not provided, a very reliable counting by the evaluating device 90 becomes possible.

FIGS. 4a to 4e show different variants of the pressure chamber 52 and of the membrane 60 sealing off the pressure chamber. Represented by dashed lines in each instance is the shape of the membrane in the deflected state.

Figure 4A:
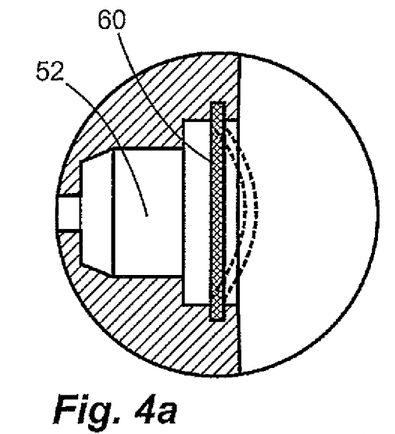

In the design according to FIG. 4a a membrane 60 finds application which is conductive as a whole and which has preferentially been encapsulated, by injection molding, by wall portions of the housing 20 that have been manufactured from a non-conductive plastic. The membrane 60 shown in FIG. 4a, which is conductive as a whole, can be obtained by an intrinsically conductive plastic. It is also possible to make an inherently non-conductive plastic conductive by means of additives/fillers. Incorporated metallic particles, for example, enter into consideration for this.

Figure 4B:
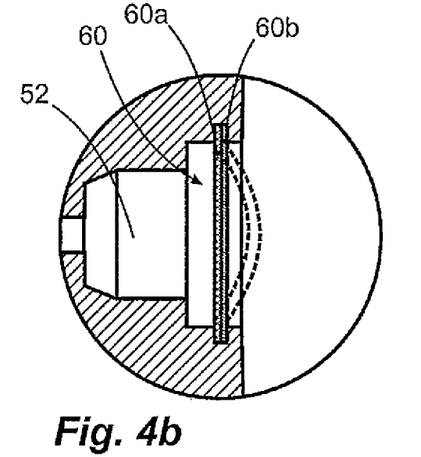

In the variant according to FIG. 4b the membrane 60 is formed in two layers. One layer 60a of the membrane pointing toward the pressure chamber consists of non-conductive plastic and serves, in particular, as an elastically deformable carrier for the outside layer 60b which is electrically conductive, for example because it consists of conductive metal. The two layers 60a, 60b may be layers produced in isolation which were assembled to form a composite membrane. It may also be expedient to produce such a membrane by the conducting layer 60b being deposited on the carrier layer 60a, for example by vapor deposition.

In the configuration shown in FIG. 4c, once again a membrane 60 which is conductive as a whole is provided, the special feature of which, however, consists in the fact that a centric region 61 of this membrane is surrounded by an annular thickening 62. This results in a stiffening which exerts an influence on the shape of the membrane 60 in the deflected state. As can be gathered from FIG. 4c, the centric region 61 is deflected in largely undeformed manner by virtue of such a stiffening. This makes it easier to create a reliably detectable planar contact of the membrane 60 with the two contact surfaces 72, 74.

Figures 4C, 4D:
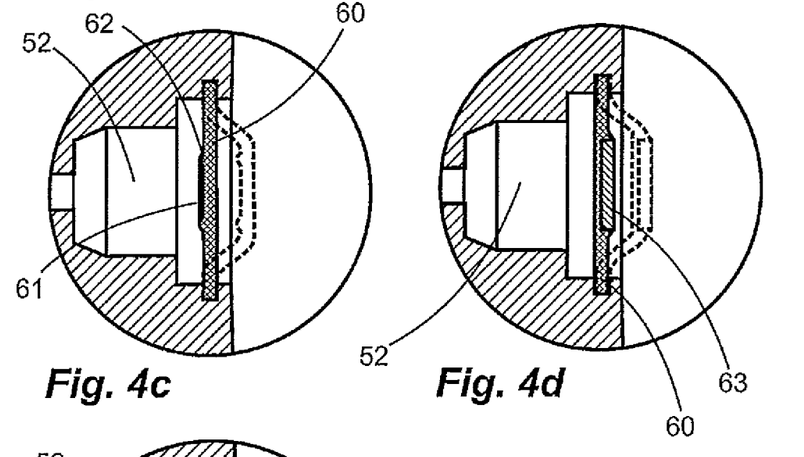

The configuration shown in FIG. 4d exhibits, in a manner similar to that shown in FIG. 4b, a membrane having portions made of different materials. However, the conductive region of the membrane here has not been created by a membrane layer covering the entire membrane but rather by a connecting portion 63 provided only centrically on the membrane 60, which, for example, may have been formed in the manner of a small metallic lamina. This metallic lamina 63 may have been adhesion-bonded to an elastically deflectable portion of the membrane or, instead of this, may have been embedded in said portion. An advantageous stiffening is also achieved by this means.

Figure 4E:
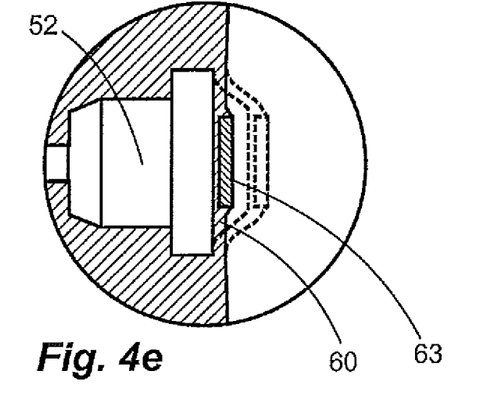

FIG. 4e is a variant in relation to the design shown in FIG. 4d. Here too, a metallic lamina 63 finds application. The special feature in the case of the configuration according to FIG. 4e consists in the fact that the membrane 60 is, moreover, formed in one piece with the surrounding portions of the housing 20 and consists of identical material. Only by virtue of the thin-walled nature of the membrane is the desired deflection capability achieved.

In addition to the variants represented, a large number of combinations are also conceivable.

Furthermore, in addition to the one-piece nature of the membrane or of portions of the membrane with the surrounding housing according to FIG. 4e, it is also possible to use, instead of the identical materials used therein for the membrane and the surrounding housing, different materials which are assembled by material closure and intimately in the two-component injection molding process. This presents itself, in particular, when utilizing electrically conductive plastics for the membrane, as is provided in the case of FIGS. 4a and 4c.

Figure 5A:
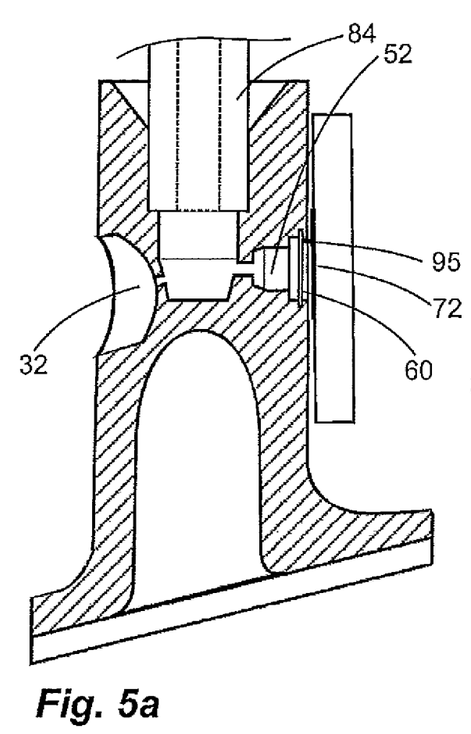
Figure 5B:
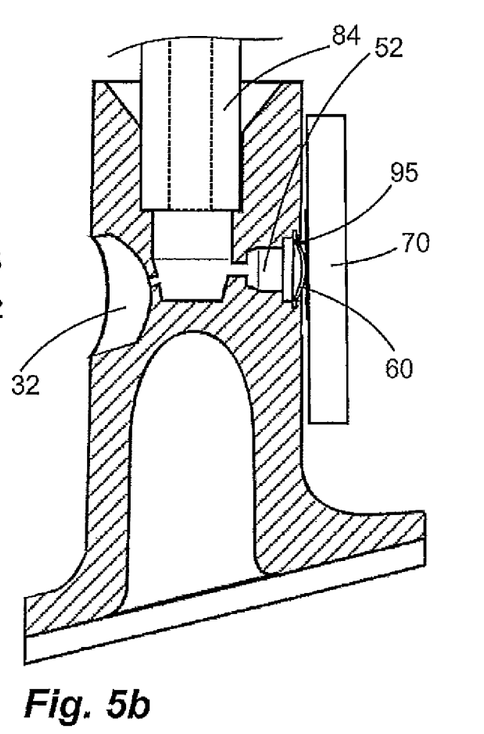
Figure 6:
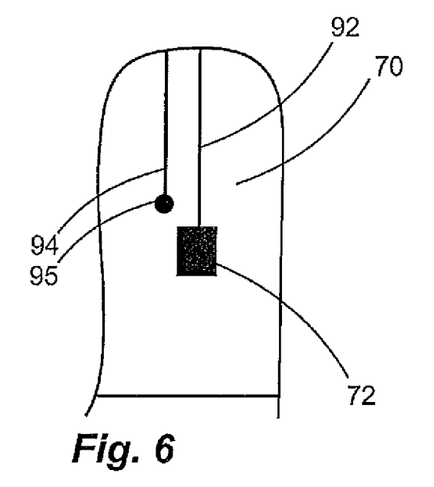

FIGS. 5a to 6 show an alternative design. In this alternative design, only one contact surface 72, which is connected to signal line 92, is provided on the printed circuit board 70. The other signal line 94, on the other hand, is permanently connected via a short connecting portion 95 to the membrane 60 which may have been formed in the same manner as shown in FIGS. 4a to 4e. The contact, which is detected by the evaluating device 90 for the purpose of counting the discharge processes, is consequently created immediately between the membrane 60, on the one hand, and the contact surface 72 on the other hand. By this means, it becomes possible to configure the contact surface 72 to be comparatively large and uninterrupted, so that further enhanced reliability is achieved with regard to the galvanic coupling of the signal lines 92, 94 achieved by membrane deformation.

The invention claimed is:

1. A pharmaceutical dispenser comprising:
   a housing,
   a medium reservoir,
   a discharge opening,
   a connecting duct which connects the medium reservoir to the discharge opening, and a detection device which is arranged in a region of the connecting duct and is designed to detect a medium flowing in the connecting duct, wherein:

the connecting duct is connected in communicating manner to a pressure chamber, the detection device includes a membrane which bounds the pressure chamber at least intermittently, includes an electrically conductive connecting portion and is capable of being pressurized by a rise in pressure in the pressure chamber and is thereby capable of being deflected together with the electrically conductive connecting portion, the detection device exhibits at least one electrical mating contact surface, with respect to which the electrically conductive connecting portion of the membrane is capable of being displaced by application of pressure, so that an electrical contact between the electrically conductive connecting portion and the at least one electrical mating contact surface is created or broken, and the membrane is formed in multiple layers and comprises at least a plastic layer and a flexible electrically conductive connecting layer which forms the electrically conductive connecting portion.

2. The pharmaceutical dispenser as claimed in claim 1, further including:

an electronic evaluating device in the form of an electronic counter, which is provided with two signal lines, a connection of which or a disconnection of which from the evaluating device performs an evaluating or counting process.

3. The pharmaceutical dispenser as claimed in claim 2, wherein:

the detection device exhibits two electrical mating contact surfaces which are connected to the two signal lines of the electronic evaluating device, are arranged to be fixed in relation to one another and are capable of being connected to one another or disconnected from one another by the deflection of the electrically conductive connecting layer.

4. The pharmaceutical dispenser as claimed in claim 2, wherein:

the at least one electrical mating contact surface is connected to one of the signal lines and the electrically conductive connecting portion is permanently connected to the other signal line.

5. The pharmaceutical dispenser as claimed in claim 1, wherein:

surrounding walls of the pressure chamber and/or of the connecting duct, which are non-deflectable as intended, and the membrane have been manufactured in one piece and from matching plastic or have been manufactured in one piece and by multi-component injection molding.

6. The pharmaceutical dispenser as claimed in claim 1, wherein:

the membrane exhibits regions of different thickness, or the membrane is provided with at least one bead or intermittent thickening.

7. The pharmaceutical dispenser as claimed in claim 1, wherein:

the dispenser takes the form of an inhalation dispenser which is designed as the housing with a receptacle for inserting an interchangeable container unit which contains the medium reservoir.

8. The pharmaceutical dispenser as claimed in claim 1, wherein:

the electrically conductive connecting layer has a thickness substantially equal to or smaller than the thickness of the plastic layer with the thickness being in a direction of movement of the plastic layer when displaced.

9. The pharmaceutical dispenser as claimed in claim 1, wherein:

the electrically conductive connecting layer extends over an entire surface of the plastic layer.

10. The pharmaceutical dispenser as claimed in claim 1, wherein:

the at least one electrical mating contact surface is two metallic electrical mating contact surfaces, and whereby several component portions of the metallic electrical mating contact surfaces are immediately adjacent each other.

11. A pharmaceutical dispenser comprising:

a housing, a medium reservoir, a discharge opening, a connecting duct which connects the medium reservoir to the discharge opening, and a detection device which is arranged in a region of the connecting duct and is designed to detect a medium flowing in the connecting duct, wherein:

the connecting duct is connected in communicating manner to a pressure chamber, the detection device includes a membrane which bounds the pressure chamber at least intermittently, includes an electrically conductive connecting portion and is capable of being pressurized by a rise in pressure in the pressure chamber and is thereby capable of being deflected together with the electrically conductive connecting portion, the detection device exhibits at least one electrical mating contact surface, with respect to which the electrically conductive connecting portion of the membrane is capable of being displaced by application of pressure, so that an electrical contact between the electrically conductive connecting portion and the at least one electrical mating contact surface is created or broken, and the membrane exhibits at least one layer of an electrically intrinsically conductive plastic.

12. The pharmaceutical dispenser as claimed in claim 11, further including:

an electronic evaluating device in the form of an electronic counter, which is provided with two signal lines, a connection of which or a disconnection of which from the evaluating device performs an evaluating or counting process.

13. The pharmaceutical dispenser as claimed in claim 12, wherein:

the detection device exhibits two electrical mating contact surfaces which are connected to the two signal lines of the electronic evaluating device, are arranged to be fixed in relation to one another and are capable of being connected to one another or disconnected from one another by the deflection of the at least one layer of the electrically intrinsically conductive plastic.

14. The pharmaceutical dispenser as claimed in claim 12, wherein:

the at least one electrical mating contact surface is connected to one of the signal lines and the electrically conductive connecting portion is permanently connected to the other signal line.

15. The pharmaceutical dispenser as claimed in claim 11, wherein:
the dispenser takes the form of an inhalation dispenser which is designed as the housing with a receptacle for inserting an interchangeable container unit which contains the medium reservoir.

16. The pharmaceutical dispenser as claimed in claim 11, wherein:
the at least one electrical mating contact surface is two metallic electrical mating contact surfaces, and whereby several component portions of the metallic electrical mating contact surfaces are immediately adjacent each other.

17. A pharmaceutical dispenser comprising:
a housing,
a medium reservoir,
a discharge opening,
a connecting duct which connects the medium reservoir to the discharge opening, and
a detection device which is arranged in a region of the connecting duct and is designed to detect a medium flowing in the connecting duct,
wherein:
the connecting duct is connected in communicating manner to a pressure chamber,
the detection device includes a membrane which bounds the pressure chamber at least intermittently, includes an electrically conductive connecting portion and is capable of being pressurized by a rise in pressure in the pressure chamber and is thereby capable of being deflected together with the electrically conductive connecting portion,
the detection device exhibits at least one electrical mating contact surface, with respect to which the electrically conductive connecting portion of the membrane is capable of being displaced by application of pressure, so that an electrical contact between the electrically conductive connecting portion and the at least one electrical mating contact surface is created or broken, and
the membrane comprises a plastic that is provided with conductive filler comprising a plurality of metallic particles.

18. The pharmaceutical dispenser as claimed in claim 17, further including:
an electronic evaluating device in the form of an electronic counter, which is provided with two signal lines, a connection of which or a disconnection of which from the evaluating device performs an evaluating or counting process.

19. The pharmaceutical dispenser as claimed in claim 18, wherein:
the detection device exhibits two electrical mating contact surfaces which are connected to the two signal lines of the electronic evaluating device, are arranged to be fixed in relation to one another and are capable of being connected to one another or disconnected from one another by the deflection of the electrically conductive connecting layer.

20. The pharmaceutical dispenser as claimed in claim 18, wherein:
the at least one electrical mating contact surface is connected to one of the signal lines and the electrically conductive connecting portion is permanently connected to the other signal line.

21. The pharmaceutical dispenser as claimed in claim 17, wherein:
the dispenser takes the form of an inhalation dispenser which is designed as the housing with a receptacle for inserting an interchangeable container unit which contains the medium reservoir.

22. The pharmaceutical dispenser as claimed in claim 17, wherein:
the at least one electrical mating contact surface is two metallic electrical mating contact surfaces, and whereby several component portions of the metallic electrical mating contact surfaces are immediately adjacent each other.

\* \* \* \* \*